(12) United States Patent
Jakubowicz et al.

(10) Patent No.: US 9,709,562 B2
(45) Date of Patent: Jul. 18, 2017

(54) LATERAL FLOW ASSAY DEVICES FOR USE IN CLINICAL DIAGNOSTIC APPARATUS AND CONFIGURATION OF CLINICAL DIAGNOSTIC APPARATUS FOR SAME

(71) Applicant: Ortho-Clinical Diagnostics, Inc., Raritan, NJ (US)

(72) Inventors: Raymond F. Jakubowicz, Rush, NY (US); Randy K. Bower, Pittsford, NY (US); Joseph J. Dambra, Rochester, NY (US); Zhong Ding, Pittsford, NY (US); James E. Robinson, Rochester, NY (US); Dale R. Ryan, Fairport, NY (US); David A. Tomasso, Rochester, NY (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 0 days.

(21) Appl. No.: 15/205,029

(22) Filed: Jul. 8, 2016

(65) Prior Publication Data
US 2016/0320382 A1 Nov. 3, 2016

Related U.S. Application Data

(62) Division of application No. 13/914,678, filed on Jun. 11, 2013, now Pat. No. 9,389,228.
(Continued)

(51) Int. Cl.
*G01N 33/00* (2006.01)
*G01N 33/543* (2006.01)
(Continued)

(52) U.S. Cl.
CPC .. *G01N 33/54386* (2013.01); *G01N 35/00069* (2013.01); *G01N 35/10* (2013.01)

(58) Field of Classification Search
CPC ....... G01N 33/54386; G01N 35/00069; G01N 35/10
See application file for complete search history.

(56) References Cited

U.S. PATENT DOCUMENTS

| 3,992,158 A | 11/1976 | Przybylowicz et al. |
| 4,296,069 A | 10/1981 | Smith et al. |

(Continued)

FOREIGN PATENT DOCUMENTS

| CN | 101506656 A | 8/2009 |
| JP | 2003-98182 | 4/2003 |

(Continued)

OTHER PUBLICATIONS

Chinese Office Action for CN 201310232406-8; Dated Jan. 21, 2016; 3 pages.
(Continued)

*Primary Examiner* — Sam P Siefke
(74) *Attorney, Agent, or Firm* — Barclay Damon, LLP

(57) ABSTRACT

A lateral flow device for use in a mainframe or point-of-care clinical analyzer, in which the lateral flow device includes a planar support having at least one sample addition area and at least one reaction area disposed thereon. The sample addition area and reaction area are fluidly interconnected to one another and form at least one lateral fluid flow path. The lateral flow device is sized for retention within a storage cartridge of the analyzer defined by a hollow interior and having a plurality of lateral flow assay devices retained in stacked relation therein.

13 Claims, 16 Drawing Sheets

Related U.S. Application Data

(60) Provisional application No. 61/658,698, filed on Jun. 12, 2012, provisional application No. 61/793,657, filed on Mar. 15, 2013.

(51) Int. Cl.
*G01N 35/00* (2006.01)
*G01N 35/10* (2006.01)

(56) References Cited

U.S. PATENT DOCUMENTS

| | | |
|---|---|---|
| 5,073,342 A | 12/1991 | Porte et al. |
| 5,419,871 A | 5/1995 | Muszak et al. |
| 6,372,542 B1 | 4/2002 | Martin et al. |
| 6,733,682 B1 | 5/2004 | Björkman et al. |
| 6,811,736 B1 | 11/2004 | Öhman et al. |
| 6,884,370 B2 | 4/2005 | Öhman et al. |
| 7,250,303 B2 | 7/2007 | Jakubowicz et al. |
| 7,312,084 B2 | 12/2007 | Jakubowicz et al. |
| 7,855,084 B2 | 12/2010 | Jakubowicz et al. |
| 8,263,024 B2 | 9/2012 | Wan et al. ............ 422/503 |
| 8,877,142 B2 | 11/2014 | ÖHman et al. |
| 2003/0003591 A1 | 1/2003 | LaCourt et al. |
| 2003/0022380 A1 | 1/2003 | Jakubowicz et al. ......... 436/54 |
| 2005/0042766 A1 | 2/2005 | Ohman et al. |
| 2006/0239859 A1 | 10/2006 | Ohman et al. |
| 2006/0285996 A1 | 12/2006 | Ohman et al. |
| 2009/0093065 A1* | 4/2009 | Ding ................. B01L 3/022 436/180 |
| 2010/0178204 A1 | 7/2010 | Yin et al. |

FOREIGN PATENT DOCUMENTS

| | | |
|---|---|---|
| JP | 2010-533490 | 10/2010 |
| JP | 2010-539453 | 12/2010 |
| WO | WO 03/103835 A1 | 12/2003 |
| WO | WO 2005/089082 A2 | 9/2005 |
| WO | WO 2005/118139 A1 | 12/2005 |
| WO | WO 2006/137785 A1 | 12/2006 |
| WO | WO 2007/149042 A1 | 12/2007 |
| WO | WO 2009/035981 A1 | 3/2009 |
| WO | WO 2009/054870 A2 | 4/2009 |

OTHER PUBLICATIONS

Japanese Office Action for JP 2013-122482; Dated: Apr. 4, 2017; 7 pages.

* cited by examiner

LATERAL FLOW ASSAY DEVICES FOR USE IN CLINICAL DIAGNOSTIC APPARATUS AND CONFIGURATION OF CLINICAL DIAGNOSTIC APPARATUS FOR SAME

CROSS REFERENCE TO RELATED APPLICATIONS

This application is a divisional application of U.S. application Ser. No. 13/914,678, filed Jun. 11, 2013 pursuant to applicable portions of 35 U.S.C. §120. U.S. application Ser. No. 13/914,678 is further based upon the following two (2) provisional applications claiming priority based on 35 USC §119(e): U.S. Ser. No. 61/658,698, filed Jun. 12, 2012 and U.S. Ser. No. 61/793,657, filed Mar. 15, 2013. The entire contents of each above-noted application is herein incorporated by reference.

TECHNICAL FIELD

This application generally relates to the field of analytical chemistry and more particularly to a lateral flow assay device to permit its use in conjunction with an automated clinical diagnostic apparatus and an automated clinical diagnostic apparatus that supports lateral flow assay devices to permit coordinated testing thereof, either alone, or in combination with other analytical test elements and chemistry systems.

BACKGROUND

Current automated laboratory instruments for the analysis of immunoassays are relatively complex, difficult to use, have lower reliability than their general chemistry counterparts, and have high production costs due to the many mechanisms that are typically required for assay processing. These assay processing mechanisms include those involving wet reagent storage with strict storage conditions, those that perform precise incubation, mechanisms to wash unbound materials effectively, as well as mechanisms for precise metering of assay and signal reagents and precise measurement of very low levels of signal.

To that end, many high volume immunoassay systems utilize micro-plates, individual wells or cuvettes either with solid phase coatings that capture antibody reactions to the walls of the vessel or with coated magnetic particles that capture antigens in solution and then are pulled to the walls by magnetic force. These systems must store wet reagents for long periods of time and under well controlled environmental conditions. Current technology is usually limited to single test measurements or are used with a test "cocktail" in which the measurement of multi-analytes is measured in total. No real multiplexing capability presently exists for assay specific measurement. The large liquid volume of expensive rare reagents used in standard immunoassay tests has significant impact to the cost of testing. Immunochemistry is also procedurally complex requiring frequent calibration, an understanding of the complex operations, and tight control of reagent storage conditions.

There has been significant evolution in terms of eliminating certain hardware from automated "wet" chemistry analytical systems. For example, U.S. Pat. No. 7,250,303 to Jakubowicz et al., describes a combinational analyzer in which pluralities of disposable metering tips are used in order to eliminate wash modules and on board fluidic systems that were previously required. This elimination of hardware enabled integration of the above noted wet chemistry hardware with additional systems for permitting the testing of so-called dry slide or thin film analytical test elements within the same apparatus. These latter analytical test elements, as generally described by U.S. Pat. No. 3,992,158 to Przbylowicz et al., are generally defined by an integral multi-layered support structure onto which sample fluid can be added and in which results can be obtained to detect various changes in the condition of the sample to yield analytical results. The above noted test elements are relatively compact and therefore a plurality of these elements can be stored for use on board an automated analyzer, such as the above-noted version. In this analyzer, a predetermined volume of sample fluid is added from a sample supply using a metering mechanism having a proboscis wherein the sample is dispensed onto the slide test element at a dispensing station of the analyzer. Upon dispensing, the sample is affected by a porous spreading layer relative to a reagent layer of the slide element in which an analyte of interest can react. The slide element includes the reagent layer as well as a reflective intermediate layer, wherein reaction results can be detected through a change in electromagnetic radiation or through a colorimetric change, by way of example.

According to the above reference and following the addition of a predetermined volume of patient sample, the slide elements are incrementally shuttled into an incubator that is defined by a set of concentric rings, the rings being independently rotatable about a center axis. The slide elements are caused to pass through an ion selective electrode station and/or a colorimetric station provided on separate rings of the incubator. A wash module can also be optionally included in the center of the incubator or elsewhere within the automated clinical analyzer, as needed.

Following incubation/test, the slide elements can be disposed of by shuttling them into an exit chute or other similar waste port. Significant throughput has been achieved using dry slide test element technology in regard to certain analyte tests that are amenable to this format. The addition of immunoassays expands the overall menu of tests that can be handled, including those requiring a plurality of tests to be performed on a single sample as performed in a test cuvette or similar form of assay supporting structure.

As noted, the use of so-called "wet" chemistry technology for the conduction and detection of immunoassays, though providing good throughput and satisfactory test results, is relatively limited given the overall expense and complexity involved. As a result, there is a general need in the field to provide additional assay measurement/analysis techniques that reduce overall complexity while further enabling the capability of performing multiple tests on a single element.

SUMMARY

According to a first aspect, there is provided a lateral flow device for use in an automated clinical analyzer, said lateral flow device comprising a planar support having at least one sample addition area and at least one reaction area disposed thereon, said areas being fluidly interconnected to one another and forming at least one lateral fluid flow path, said lateral flow device being sized for retention within a storage cartridge defined by a hollow interior and having a plurality of said lateral flow assay devices retained in stacked relation.

According to at least one version, the lateral flow assay device further includes at least one detection area and at least one wicking area, each of these areas being formed on said support and fluidly connected to the at least one sample addition area and said at least one reaction area along the at least one lateral fluid flow path.

In one version, a plurality of vertically extending projections are formed on a top surface of the support. The plurality of projections are preferably dimensionally sized and spaced in relation to one another to facilitate lateral capillary flow along said at least one lateral fluid flow path. In one embodiment, the plurality of projections are dimensionally sized and spaced in relation to one another to spontaneously induce lateral capillary flow along the at least one lateral fluid flow path such that lateral capillary flow is induced solely based on said plurality of projections.

Various other mechanisms can be employed to further assist in promoting flow along the defined fluid path. For example and according to one version, a hydrophilic layer can be disposed over at least a portion of the wicking area of the lateral flow assay device.

According to one exemplary embodiment, the lateral flow assay device is provided with a plurality of reaction areas that are defined along the at least one lateral fluid flow path. Preferably, at least one reaction area retains at least one reagent and in which the at least one reagent is attached to projections disposed in the reaction area.

According to one version, a first reaction area is disposed in relation to the sample addition area in which the first reaction area retains a detection conjugate. Preferably, the interaction of sample and the detection conjugate produces a detectable plume, which is fluorescent or otherwise detectable.

The lateral flow assay device can include at least one flow channel disposed between said at least one sample addition area and said at least one wicking area. In one version, the plurality of projections extend upwardly from a bottom surface of the at least one flow channel and in which the flow channel extends in a folded configuration between the at least one sample addition area and the wicking area of the device. A portion of this flow channel permits alignment with a detection instrument relative to at least one detection area of the device.

According to another version, there is provided an automated clinical analyzer configured for processing a plurality of lateral flow assay devices, each of said lateral flow devices comprising a support and at least one sample addition area disposed upon said support and fluidly interconnected along at least one lateral fluid flow path, said automated clinical analyzer comprising:

a metering mechanism for dispensing sample onto a sample addition area of at least one lateral flow assay device;

an incubator assembly having means for receiving a plurality of said lateral flow assay devices; and at least one detection device for detecting results of at least one lateral flow assay device.

In one version, the lateral flow assay devices produce detectable signals based on the addition of sample to said at least one sample addition area and interaction with at least one reagent disposed on a reaction area of the device. In one exemplary version, the signals produced are fluorescent and in which the at least one detection device comprises a fluorimeter.

According to one version, the at least one incubator assembly includes at least one ring member, said at least one ring member having a plurality of receiving stations sized for receiving said plurality of lateral flow assay devices. In an exemplary embodiment, the at least one detection device is disposed on or adjacent the incubator assembly and in which the analyzer further includes at least one mechanism for selectively moving said lateral flow assay devices into and out of said incubator assembly.

Preferably, the lateral flow assay devices are stored for use on said analyzer in stacked relation in at least one storage cartridge. In one version, the automated clinical analyzer is further configured for the processing dry-slide analytical test elements and in another version is further configured for handling of wet chemistry assays. According to one embodiment, the at least one incubator assembly is configured to interchangeably handle dry-slide analytical test elements and said lateral flow assay devices. In one version of such an interchangeable apparatus, the at least one incubator assembly includes a plurality of concentric ring assemblies, each of said ring assemblies having stations for receiving one of dry-slide analytical test elements and said lateral flow assay devices. Alternatively, a first incubator assembly can be provided for handling of dry-slide analytical test elements and a second incubator assembly for handling of said lateral flow assay devices. For handling of so called "wet" immunoassays, the analyzer can further include a wet chemistry assay analytical system with either a system configured for handling of lateral flow assay devices and/or analytical dry slide elements.

As to the lateral flow assay devices themselves for use in the analyzer and according to a preferred version, the lateral flow assay device further comprise at least one detection area and at least one wicking area, each of said areas being formed on said support and fluidly connected to said at least one sample addition area and said at least one reaction area along said at least one lateral fluid flow path.

In one version, a plurality of vertically extending projections are formed on a top surface of the support. The plurality of projections are preferably dimensionally sized and spaced in relation to one another to facilitate lateral capillary flow along said at least one lateral fluid flow path. In one embodiment, the plurality of projections are dimensionally sized and spaced in relation to one another to spontaneously induce lateral capillary flow along the at least one lateral fluid flow path wherein the device can be designed such that lateral capillary flow is induced along at least one said lateral fluid flow path solely based on said plurality of projections.

Various other mechanisms can be employed to further assist in flow. For example and according to one version, a hydrophilic layer can be disposed over at least a portion of the wicking area of the lateral flow assay device.

According to one exemplary embodiment, each lateral flow assay device is provided with a plurality of reaction areas that are defined along the at least one lateral fluid flow path to enable a plurality of tests to be conducted on a single device. Preferably, at least one reaction area retains at least one reagent and in which the at least one reagent is attached to projections in the reaction area.

According to one version, a first reaction area is disposed in relation to the sample addition area in which the first reaction area retains a detection conjugate. Preferably, the interaction of sample and the detection conjugate produces a detectable plume, which is fluorescent or otherwise detectable.

The lateral flow assay device can include at least one flow channel disposed between said at least one sample addition area and said at least one wicking area. In one version, the plurality of projections extend upwardly from a bottom surface of the at least one flow channel and in which the flow channel extends in a folded configuration between the at least one sample addition area and the wicking area of the device. A portion of this flow channel permits alignment with the detection device of the analyzer relative to at least one detection area. In that regard, a reading station is disposed in relation to the detection device, this reading station having features for aligning a lateral flow assay device to the detection instrument to permit coordinated reading of the device in a repeatable manner.

According to yet another aspect, there is provided an automated analyzer comprising: storage cartridges for separately retaining a first plurality of analytical test elements and a second plurality of analytical test elements, in which the first plurality of analytical test elements comprise thin-film slide elements and said second plurality of analytical test elements comprise lateral flow assay devices; a metering mechanism for dispensing sample onto a sample addition area of each of said first and second plurality of analytical test element; at least one incubator assembly having means for receiving said analytical test elements; and at least one detection device for detecting results relative to each of said analytical test elements.

According to at least one version, the least one said incubator assembly is configured to interchangeably handle the first and said second plurality of test elements. In one embodiment, the incubator assembly includes a plurality of concentric rings having receiving stations for receiving a test element, and in which each ring is configured to interchangeably receive each of said first and second plurality of test elements. In another version thereof, the incubator assembly includes a plurality of concentric rings and in which at least one said ring is configured to handle one of said first and second pluralities of test elements and the another said ring is configured to handle the other of said pluralities of test elements.

In one embodiment, the lateral flow assay devices comprise a support having said at least one sample addition area and at least one reaction area and in which said device produces a fluorescent signal. The analyzer includes a detection instrument for detecting the fluorescent signal produced by said lateral flow assay devices.

According to another version, the analyzer can be further equipped to include a wet chemistry module or analytical system configured for performing immunoassays and/or chemistry assays.

According to yet another aspect, there is provided a method for processing analytical test elements in an automated clinical analyzer, said method comprising the steps of: introducing a first plurality of analytical test elements into said automated clinical analyzer, said first plurality comprising lateral flow assay devices each comprising a support, at least one sample addition area and a defined lateral fluid flow path that includes at least one reaction area; dispensing a volume of sample onto at least one said lateral flow assay device; incubating said at least one lateral flow assay device; and detecting at least one test result from said at least one lateral flow assay device.

In one embodiment, the introducing step can include the step of loading a storage cartridge, retaining a plurality of said lateral flow assay devices in stacked relation, into the automated analyzer.

According to one version, the dispensing step includes the step of aspirating a quantity of sample from a sample supply of said analyzer using a metering mechanism and dispensing at least a portion of said aspirated sample onto a sample addition area of said lateral flow assay device.

In one embodiment, the incubating step includes the step of shuttling said lateral flow assay device from a dispensing station into a receiving station of said incubator. In one preferred version, the shuttling step is performed by a reciprocating pusher blade assembly.

According to one exemplary embodiment, each of the lateral flow assay device includes a plurality of projections extending upwardly from a top surface of said support, said plurality of projections having a center to center spacing and having height and diameter dimensions configured to enable capillary flow of sample applied to said sample addition area. Preferably, each lateral flow assay device further comprises at least one sample addition area, at least one reaction area and at least one wicking area, each of said areas being fluidly interconnected and defining at least one fluid flow path and in which the lateral flow assay device produces a detectable signal, such as a fluorescent signal. In one preferred version, the detecting step includes the additional step of aligning the lateral flow assay device and detecting the fluorescent signal using a fluorimeter.

According to yet another version, an additional step can include introducing a second plurality of analytical test elements to the automated clinical analyzer, said second plurality comprising thin-film slide elements, said method further including the steps of dispensing a quantity of sample onto a sample addition area of said thin-film slide elements, incubating of said slide elements and detecting of at least one test result relating thereto. In one design, the first and second pluralities of analytical test elements can be handled interchangeably by the automated clinical analyzer. In another variation, an additional step includes providing a wet chemistry assay system on said automated clinical analyzer.

According to yet another aspect, a lateral flow device is provided for use in both a point-of-care analyzer and an automated clinical analyzer. The lateral flow device comprises a planar support having at least one sample addition area and at least one reaction area disposed thereon, the areas being fluidly interconnected to one another and forming at least one lateral fluid flow path, and in which the lateral flow device is capable of running on both a point-of-care analyzer and an automated clinical analyzer without modification. Preferably, the lateral flow device has the same dimensions for both point-of-care and automated clinical analyzer applications.

A number of advantages are provided by providing a lateral flow assay device for analytical purposes, as herein described.

First, a consistent format is created across all chemistries, this format being better aligned with that a of so-called "dry" chemistry format. The foregoing alignment further permits instrument simplification. Because the lateral flow assay devices described herein can coexist, for example, with current dry slide test element technology, significant reductions in size (i.e., a smallest analyzer foot print) and cost improvement are each achieved.

Still further, common reagent storage using a cartridge format, also similar to conventional dry slide test element technology, can provide users with a convenient and efficient single point for entry.

In addition, the herein described lateral flow assay devices provide test multiplexing within a single lateral flow assay device. As a result, there are a reduced number of assay protocols for simpler scheduling. This advantage can therefore obviate the need, in some instances, of an automated clinical analyzer having wet chemistry analytical systems. In fact, an analyzer can be designed that solely supports the use of lateral flow assay devices, as described herein.

Another significant advantage provided is that the herein described lateral flow assay device does not require the separate addition of wet reagents. That is, dry reagents are already incorporated into the structure of the lateral flow assay device, thereby allowing for room temperature storage of these devices and enabling extended shelf life.

Additionally, only very low sample volumes of sample and/or other fluids are required. Therefore, applications of the herein described lateral flow assay devices may include the direct use of whole blood, thereby providing reduced overall processing times in that no centrifugation is required.

Yet another direct advantage provided is that of significantly reduced turnaround time for testing. By employing the herein described lateral flow assay devices, in an automated clinical analyzer, overall reaction times that are traditionally as high as one hour can be effectively reduced to a range covering only approximately five to ten minutes. Still further, the herein described lateral flow device can be used for both automated clinical analyzer as well as point-of-care analyzer applications. Preferably, the lateral flow assay device can include the same dimensions for each type of application.

Still another advantage realized herein is that the use of the herein described lateral flow assay devices creates lower overall costs in instrumentation. Part complexity can be reduced by as much as 50%, as compared, for example, to integrated or combinational analyzers by employing the herein described lateral flow assay devices therein. For example and as noted previously, the herein described lateral flow assay devices can be stored at room temperature and therefore do not require refrigerated storage assemblies, as required by wet chemistry analytical systems. Additional savings are realized in terms of overall plastic waste, which is significantly reduced according to the present invention.

By enabling multiplexing on a single lateral flow assay device, multiple assays can be run simultaneously on a single device, thereby creating lower cost per test and significantly higher effective throughput. In fact, and approaching general chemistry throughputs, multiplexing can significantly increase throughput by the effective multiplexing factor and can be as high as 10 times (or more). In the meantime, the herein described lateral flow assay devices otherwise permit random access in terms of testing as used on an automated clinical analyzer, other than the enabled multiplexing that is permissible on a single device.

The included lateral flow assay device further can enable the incorporation of various internal controls, thereby providing at least one means to ensure calibration, quality of the result and the ability to track any assay degradation over time, each being integrated within the test element itself. These features further provide means for their incorporation with other intelligent reliability systems, such as provided on automated clinical analyzers.

Still another advantage is that of factory or wet calibration—stability that allows a factory calibration to simplify user operation. At a minimum, the foregoing increases calibration intervals to typical general chemistry intervals.

Yet still another advantage herein realized is that of commonality of formats between point-of-care (POC) and mainframe assays, providing development improvement. As such, an assay can be enabled to be used in both types of applications (POC and mainframe), providing higher production volumes and economies of scale. The foregoing therefore ensures quality results and equal performance in both the POC and mainframe markets.

Still another advantage is that thin film slide elements and lateral flow assay devices can now be simultaneously used on a single analyzer, wherein the form factor of the lateral flow assay devices permits their use interchangeably with thin film dry slide elements and using an expansive number of already existing apparatus that can easily accommodate same. Versatility is significantly enhanced wherein systems can be realized that can incorporate thin-film analytical test elements, lateral flow assay devices as described herein and conventional wet chemistry systems or portions thereof in a single unit.

These and other advantages and features will be readily apparent from the following Detailed Description, which should be read in conjunction with the accompanying drawings.

DETAILED DESCRIPTION

Figure 1:
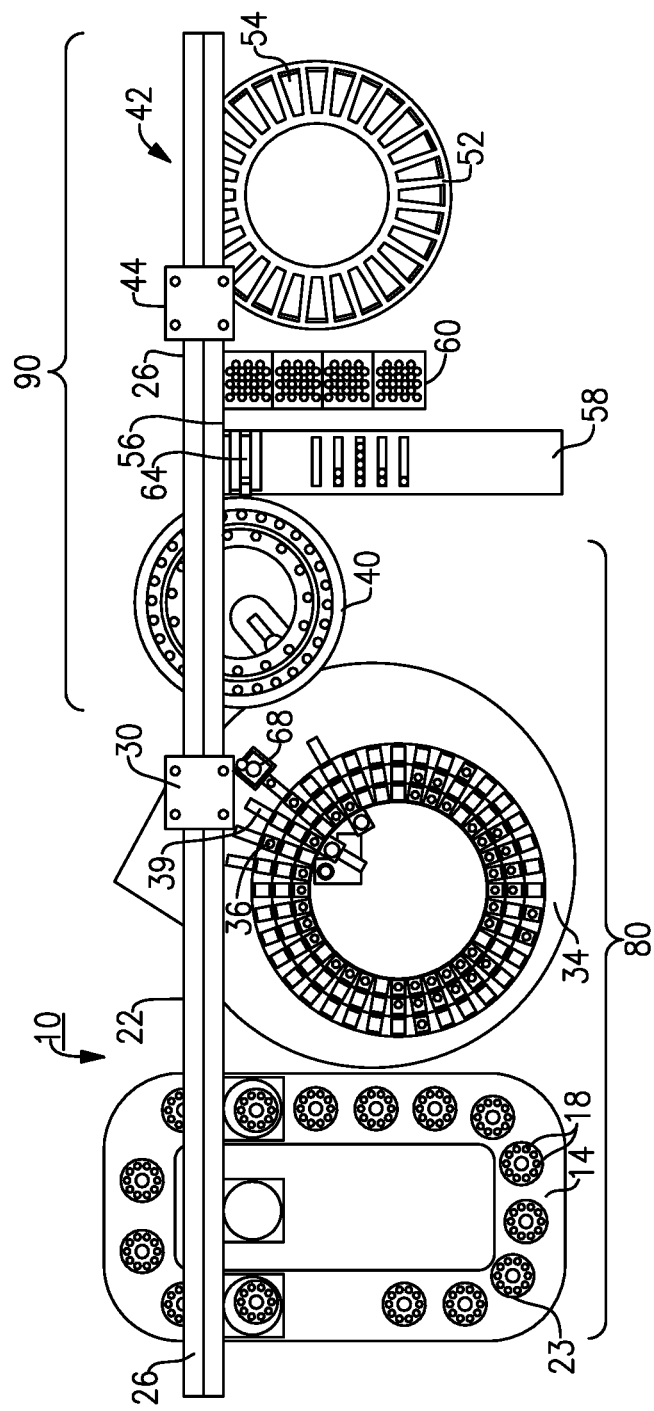
FIG. 1 depicts a top plan view, partially broken away, of a prior art automated clinical analyzer.

The following exemplary embodiment relates to the configuration and design of at least one lateral flow assay device for use in a mainframe automated clinical analyzer. More specifically, this particular embodiment describes the enablement of a plurality of lateral flow assay devices in conjunction with an automated clinical analyzer that is typically configured to receive and process dry slide analytical test elements, a lateral flow assay device that can be used in an automated clinical analyzer and a related method involving interchangeable use of dry slide test elements and lateral flow assay devices in an automated clinical analyzer. It should be noted, however, that this description is intended to be exemplary of the incorporation of certain lateral flow assay devices into an automated clinical analyzer and/or a point-of-care (POC) analyzer. To that end, it will be readily apparent to one of sufficient skill that the inventive concepts herein described are equally applicable to a myriad of other lateral flow assay device designs and use in various other types of automated, as well as POC diagnostic clinical analyzers. Still further, the automated clinical analyzers described herein can be configured, for example, to handle lateral flow assay devices without requiring the separate inclusion of dry slide analytical elements as a stand-alone assembly and alternatively to include other analytical systems in addition to those for the handling of lateral flow assay devices, as described herein, such as a conventional wet chemistry analytical system.

It should further be noted that the accompanying drawings are not necessarily presented to scale and therefore no narrowing interpretation should be made in terms of dimensions depicted.

In terms of defining certain of the terms that follow, the term "analyte" is used as a synonym of the term "marker" and intended to minimally encompass any chemical or biological substance that is measured quantitatively or qualitatively and can include small molecules, proteins, antibodies, DNA, RNA, nucleic acids, virus components or intact viruses, bacteria components or intact bacteria, cellular components or intact cells and complexes and derivatives thereof.

As used in this specification and the appended claims, the singular forms "a", "an" and "the" are intended to further include plural referents unless the context clearly dictates otherwise.

The term "about" as used in connection with a numerical value throughout the description and the claims denotes an interval of accuracy, familiar and acceptable to a person skilled in the art. The interval governing this term is preferably ±10%.

The term "sample" herein means a volume of a liquid, solution or suspension, intended to be subjected to qualitative or quantitative determination of any of its properties, such as the presence or absence of a component, the concentration of a component, etc. Typical samples in the context of the present invention as described herein are human or animal bodily fluids such as blood, plasma, serum, lymph, urine, saliva, semen, amniotic fluid, gastric fluid, phlegm, sputum, mucus, tears, stool, etc. Other types of samples are derived from human or animal tissue samples where the tissue sample has been processed into a liquid, solution, or suspension to reveal particular tissue components for examination. The embodiments of the present invention are applicable to all bodily samples, but preferably to samples of whole blood, urine or sputum.

The term "lateral flow assay device" as discussed herein refers to any device that receives fluid, such as sample, and includes a laterally disposed fluid transport or flow path along which various stations or sites are provided for supporting various reagents, filters and the like through which sample traverses under the influence of capillary or other applied forces.

The terms "automated clinical analyzer", "clinical diagnostic apparatus" or "clinical analyzer" as discussed herein, refer to any apparatus enabling the scheduling and processing of various analytical test elements, such as thin-film or "dry slide" test elements and/or lateral flow assay devices, as discussed herein and in which a plurality of test elements can be initially loaded for processing. This apparatus further includes a plurality of components/systems configured for loading, incubating and testing/evaluating a plurality of analytical test elements in automated or semi-automated fashion and in which test elements are automatically dispensed from at least one contained storage supply, such as a cartridge, without user intervention. Clinical diagnostic apparatus as defined herein can further include desktop and point of care (POC) type devices, as opposed to mainframe versions.

The terms "zone", "area" and "site" are used in the context of this description, examples and claims to define parts of the fluid flow path on a substrate, either in prior art devices or in at least one device according to an embodiment of the invention.

The term "reaction" is used to define any reaction, which takes place between components of a sample and at least one reagent or reagents on or in the substrate, or between two or more components present in the sample. The term "reaction" is in particular used to define the reaction, taking place between an analyte and a reagent as part of the qualitative or quantitative determination of the analyte.

The terms "substrate" or "support" refers to the carrier or matrix to which a sample is added, and on or in which the determination is performed, or where the reaction between analyte and reagent takes place.

Prior to discussing the inventive concepts, certain background is first provided with reference to FIG. 1 depicting one version of a known integrated or "combinational" automated clinical analyzer 100. By "combinational", what is meant is that the analyzer is equipped to handle conventional immunoassays or chemistry assays, as well as testing of thin film analytical test elements. This exemplary analyzer 10 is defined by a housing or enclosure (not shown) that is appropriately sized to retain a plurality of components that are now briefly described. Generally, the analyzer 10 is configured to commonly retain two separate analytical systems that can be used in tandem; namely, a so-called "dry" chemistry analytical system 80 and a "wet" (immunoassay-based or chemistry-based) analytical module or system 90.

More specifically, the analyzer 10 includes a primary sample supply or handler 14 that retains a plurality of primary sample containers 18 and a primary metering mechanism 22 that includes a metering transport rail 26 and a metering truck 30 which is movable along the transport rail between a number of stations. Among the stations disposed along the linear travel path of the metering mechanism 22 are a metering station 68 for a first incubator assembly 34. At this metering station 68, a quantity of sample can be deposited onto a dry slide (thin film) element 36 which is then shuttled into the first incubator assembly 34. The test element 34 is further shown in FIG. 2 and is defined by a substrate 37 having a porous center section 38 defining a multi-layered reaction area that receives a volume of sample, which is aspirated thereupon using a pipette or other dispensing apparatus. Specifics relating to this latter test component are described in greater detail in U.S. Pat. No.

3,992,158 to Przbylowicz et al., the entire contents of this reference being incorporated herein.

The first incubator assembly 34 includes at least one read station (not shown) including a testing device for correlated analyte detection, such as a reflectometer or an electrometer (not shown). According to this version, an auxiliary sample handling apparatus 40 is disposed in relation to the first incubator assembly 34 and includes a tip supply for maintaining a plurality of disposable metering tips. The foregoing comprises the dry chemistry analytical system 80 of this analyzer 10.

Still referring to FIG. 1, a secondary metering mechanism 42 includes a secondary metering mechanism having a metering truck 44 similar to the metering truck 30 for the dry chemistry portion 80 of the analyzer 10, which is also movable along the metering transport rail 26, a reagent wheel 52 which includes a plurality of reagent containers or packs 54 containing at least one reagent, a second incubator assembly 56, a micro-tip supply 60, and a reaction vessel conveyor 58 carrying a plurality of reaction vessels 64. Each of the foregoing components define the wet chemistry portion 90 of the analyzer 10.

As noted, each of the dry and wet chemistry systems 80, 90 are integrated. In operation, a plurality of unsealed disposable metering tips are initially loaded from a tip supply (not shown) into stations that are provided on the auxiliary sample handling apparatus 40. The movable truck 30 of the primary metering mechanism 22 is shuttled along the metering transport rail 26 to a predetermined station that enables a tip to be picked up using the probocsis thereof in a commonly known manner. The movable truck 30 is then driven to the primary sample handler 14 and the probocsis and attached metering tip are lowered into an aligned sample receptacle 18. A predetermined volume of sample is drawn under vacuum and aspirated into the confines of the metering tip. The metering truck 30 carrying the metering tip with aspirated sample is then shuttled along the transport rail 26 from the primary sample handler 14 to the metering station 68. At this station 68, a dry slide (thin film) analytical test element 36 has been positioned as discharged from a vertically disposed storage cartridge (not shown) carrying a plurality of these elements.

A volumetric portion of the sample contained within the metering tip is then dispensed onto the dry slide test element 36, which is arranged to be loaded using pusher blade assembly 39, into the first incubator assembly 34. The sample is metered onto, for example, a potentiometric or colorimetric slide element which is then incubated for a predetermined time, in which the provided test instrumentation determines the results (analyte concentration, detection, etc.). Additional details relating to the incubation and testing of dry slide elements are described, for example, in U.S. Pat. No. 4,296,069, incorporated by reference in its entirety herein.

Sequentially and following the above-noted metering step according to this known version, the metering tip is then advanced to the auxiliary sample handling apparatus 40. At this apparatus 40, the dispense end of the metering tip is heat-sealed enabling the metering tip to thereafter be used as an auxiliary sample container for use with the wet chemistry system 90. The sealed metering tip is retained within a housing in relation to the secondary metering mechanism 42 wherein a plurality of sealed metering tips are stored.

As to the conduction of "wet" assays and if sample is required, a micro-tip is picked up from the micro-tip supply 60 by the secondary metering mechanism 42 using the metering truck 44 and the attached proboscis (not shown). The micro-tip is sized to fit within the confines of a sealed metering tip serving as an auxiliary sample retainer. The metering truck 44 is then moved into position relative to the auxiliary sample supply 40. Once sample has been aspirated from the auxiliary sample retainer (sealed metering tip), the movable metering truck 44 is located in relation to a reaction vessel 64, and specifically a reaction chamber thereof for dispensing of the sample. An exemplary reaction vessel is described in U.S. Patent Application Publication No. 2003/0003591A1, the entire contents of which are herein incorporated by reference. Once sample has been dispensed into a reaction chamber of the reaction vessel 64, the micro-tip can be discarded by the apparatus.

Reagents for the conducted wet assay are brought to the reaction vessel 64 from the reagent container 54, which is rotated to a predetermined aspiration position by the reagent wheel 52 that retains the separate reagent containers 54 in a refrigerated state. An unsealed metering tip is picked up using the probocsis by the movable metering truck 44 of the secondary metering mechanism 42. The movable truck 44 is then shuttled to an aspiration position of the reagent wheel 52. In this position, reagent fluid is aspirated into the attached metering tip. The metering truck 44 is then shuttled to a metering position relative to the reaction vessel 64 and reagent is dispensed into the reaction chamber. The tip can actually be fitted within the reaction chamber containing the sample to aid in mixing of reagent and sample, if needed. The metering tip is subsequently disposed of following its use. Additional quantities of other reagents or other fluids (e.g., calibration, dilution, wash, etc.) are similarly handled using disposable metering tips for conducting the assay, which is subsequently incubated in the incubator 56 including a read station (not shown) having a detection instrument disposed therein, such as a spectrophotometer, for obtaining results. Additional background and detail in regard to integrated or so-called "combinational" automated clinical analyzers, such as those described according to FIG. 1 and variants thereof, is provided for example in U.S. Pat. Nos. 7,250,303 and 7,855,084B2, herein incorporated by reference in their entirety.

Figure 3:
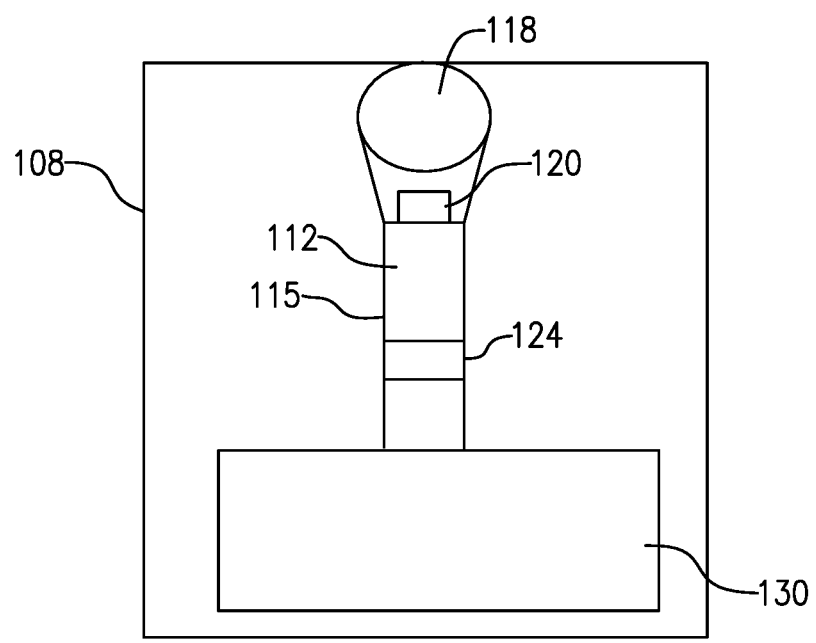
FIG. 3 is a top plan view of a known lateral flow assay device.

With the foregoing background and now referring to FIG. 3, a known exemplary lateral flow assay device 100 for purposes of this embodiment is herein described. The lateral flow assay device 100 in accordance with this embodiment is defined by a planar substrate 108 preferably made from a suitable non-porous material, though porous materials can be alternatively provided, as discussed infra. A plurality of projections 112, such as micropillars, extend upwardly from a top or upper surface of the substrate 108 the projections preferably forming the defined area shown by the bordering line 115. In other versions and as discussed in a later section, flow channels can be cut into the surface of the substrate in which the projections extend from a bottom surface of the channel. According to this particular assay device design, a sample addition area 118 at one side of the device 100 extends to an adjacent reagent zone 120 disposed in relation to the sample addition area, further extending at least one detection area 124 and a wicking area 130.

A defined fluid flow path is created from the sample addition area 118 extending to the wicking area 130 that is at least partially open. In another embodiment, the flow path is entirely open. By "open" what is meant is that there is no lid or cover at a capillary distance. Thus a lid, if present as a physical protection for the flow path, does not contribute to the capillary flow in the flow path. An open lateral flow path is described, for example, in the following published applications: WO 2003/103835, WO 2005/089082; WO 2005/118139; WO 2006/137785; and WO 2007/149042, all of which are incorporated by reference in their entireties. The extending projections 112 have a height (H), diameter (D) and a distance or distances between the projections (t1, t2) such, that lateral capillary flow of an applied fluid, such as plasma, preferably human plasma, in the zone is achieved. These relationships are discussed in US 2006/0285996, which is incorporated by reference in its entirety. In addition to optimizing the above-mentioned height, diameter and a distance or distances between the projections, the projections 112 may be given a desired chemical, biological or physical functionality, e.g. by modifying the surface of the projections for purposes, for example, of the reagent area(s) and detection area(s) of the device. In one embodiment, the projections have a height in the interval of about 15 to about 150 µm, preferably about 30 to about 100 µm, a diameter of about 10 to about 160 µm, preferably 40 to about 100 µm, and a gap or gaps between the projections of about 3 to about 200 µm, preferably 5 to 50 µm or 10 to about 50 µm from each other. The flow channel between the sample addition area 118 and the wicking area 130 may have a length of about 5 to about 500 mm, preferably about 10 to about 100 mm, and a width of about 0.3 to about 10 mm, preferably about 0.3 to about 3 mm, preferably about 0.5 to 1.5, and preferably about 0.5 to 1.2 mm. The projections 112 according to this device design are substantially cylindrical in configuration and cross section. However, their specific design can easily be varied to those of different shapes (e.g., rhombic, hexagonal, etc) and sizes to augment flow, as well as to filter materials.

Figure 4:
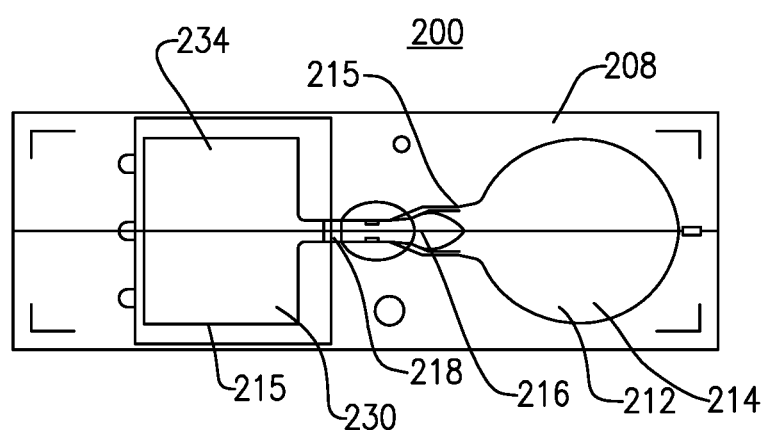
FIG. 4 depicts a top plan view of another known lateral flow assay device.

Referring to FIG. 4, there is depicted another known lateral flow assay device 200 is defined by a non-porous substrate 208 having a sample addition area or zone 214 disposed at one end that forms a portion of a lateral fluid flow path extending through a reagent zone 216 containing a detection conjugate or other reagent and further extending to a detection zone 218 and further extending to a wicking zone 230 defining the opposite end of the fluid flow path. Optionally, the lateral fluid flow path may also include additional separate zones containing reagents or detection conjugate, as well other zones, areas or sites along this path that can be utilized used for washing of the sample and any bound or unbound components thereof.

According to this particular embodiment, a plurality of projections 212 extend upwardly from the top surface of the substrate 208 substantially defining the active portions defined within the bordering line 215 of this device wherein the projections are specifically designed dimensionally in terms of their height and diameters, as well as with relative interpillar spacings, so as to solely promote spontaneous lateral capillary flow along the defined fluid flow path between the sample addition area 214 and the wicking zone 230. As discussed infra, this design is referred to as an "open" system or device, meaning that side walls and a cover are not necessarily required to assist in the creation of capillary force. It will further be noted that a cover or lid can be optionally included; for example, a cover can be added to the device as needed, the cover being spaced in relation to the projections 212 so as not contribute to the lateral capillary flow of a sample liquid. It is has been determined, however, that the addition of a hydrophilic foil or layer 234 directly onto at least a portion of the wicking area 230 alone does contribute to the overall flow rate (process time) of an aspirated sample.

Figure 5:
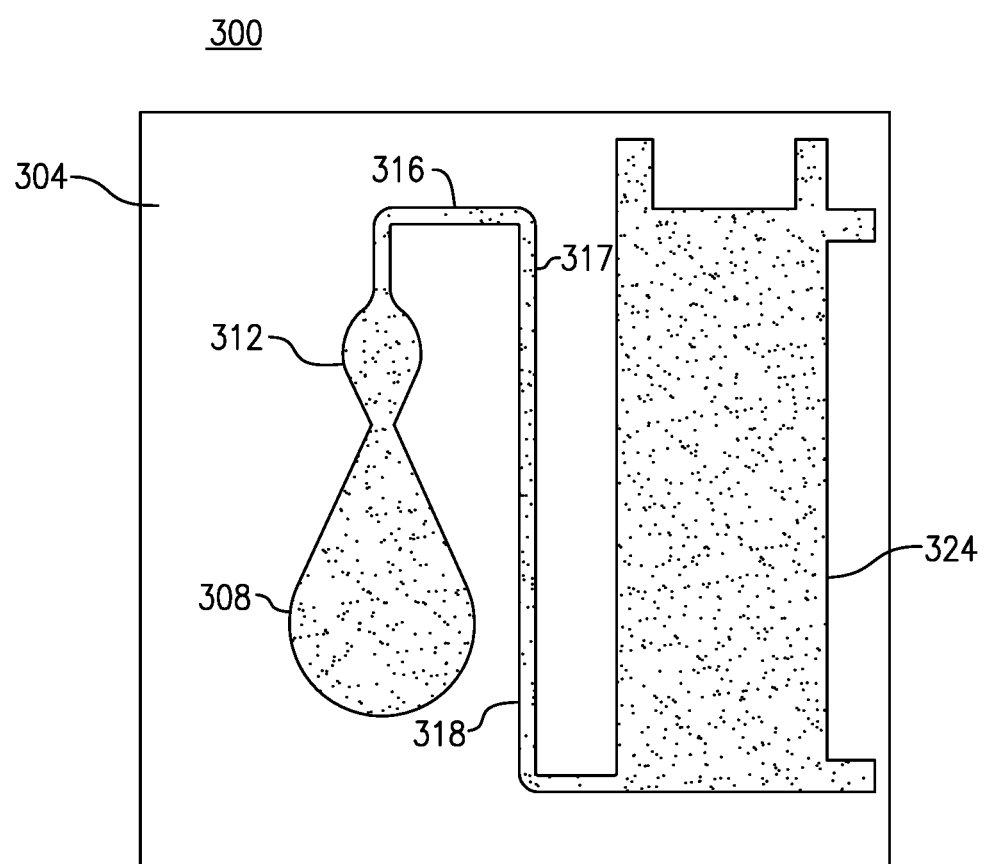
FIG. 5 is a top plan view of a lateral flow assay device made in accordance with an exemplary embodiment.

An exemplary design of another lateral flow assay device 300, which is herein described for purposes of the present invention is provided in FIG. 5. Though this particular assay device 300 is referred to throughout the remainder of this description in terms of an exemplary embodiment, it will be readily apparent that other device designs and possible variants of these designs could also be similarly configured for interrelationships in a clinical analyzer, as herein discussed. The exemplary assay device 300 is defined by a substrate 304 that includes a liquid sample addition zone 308 that receives sample from a liquid dispenser. The sample is typically deposited onto the top of the zone. The sample addition zone 308 is capable of transporting the liquid sample from the point when the sample is deposited to a reagent zone 312, through an optional filter and reagent addition zone (not shown), preferably through capillary flow. The capillary flow inducing structure can include porous materials, such as nitrocellulose, or preferably through projections, such as micro-pillars as previously described. A filler material (not shown) can be also be placed within the sample addition zone 308 to filter particulates from the sample or to filter blood cells from blood so that plasma can travel through the device 300.

Located between the sample addition zone 308 and a detection zone 318 is a reagent zone 312. The reagent zone 312 can include reagent(s) integrated into this analytical element and are generally reagents useful in the reaction—binding partners such as antibodies or antigens for immunoassays, substrates for enzyme assays, probes for molecular diagnostic assays, or are auxiliary materials such as materials that stabilize the integrated reagents, materials that suppress interfering reactions, and the like. Generally, one of the reagents useful in the reaction bears a detectable signal as discussed herein. In some cases, the reagents may react with the analyte directly or through a cascade of reactions to form a detectable signal such as a colored or fluorescent molecule. In one preferred embodiment, the reagent zone includes conjugate material. The term "conjugate" means any moiety bearing both a detection element and a binding partner.

For purposes of this description, a detection element is an agent which is detectable with respect to its physical distribution and/or the intensity of the signal it delivers, such as but not limited to luminescent molecules (e.g., fluorescent agents, phosphorescent agents, chemiluminescent agents, bioluminescent agents and the like), colored molecules, molecules producing colors upon reaction, enzymes, radioisotopes, ligands exhibiting specific binding and the like. The detection element also referred to as a label is preferably chosen from chromophores, fluorophores, radioactive labels and enzymes. Suitable labels are available from commercial suppliers, providing a wide range of dyes for the labeling of antibodies, proteins and nucleic acids. There are, for example, fluorophores spanning practically the entire visible and infrared spectrum. Suitable fluorescent or phosphorescent labels include for instance, but are not limited to, fluoroceins, Cy3, Cy5 and the like. Suitable chemoluminescent labels include but are not limited to luminal, cyalume and the like.

Similarly, radioactive labels are commercially available, or detection elements can be synthesized so that they incorporate a radioactive label. Suitable radioactive labels include but are not limited to radioactive iodine and phosphorus; e.g., $^{125}$I and $^{32}$P.

Suitable enzymatic labels include but are not limited to horseradish peroxidase, beta-galactosidase, luciferase, alkaline phosphatase and the like. Two labels are "distinguishable" when they can be individually detected and preferably quantified simultaneously, without significantly disturbing, interfering or quenching each other. Two or more labels may be used, for example, when multiple analytes or markers are being detected.

The binding partner is a material that can form a complex that can be used to determine the presence of or an amount of an analyte. For example, in a "sandwich" assay, the binding partner in the conjugate can form a complex including the analyte and the conjugate and that complex can further bind to another binding partner, also called a capture element, integrated into the detection zone. In a competitive immunoassay, the analyte will interfere with binding of the binding partner in the conjugate to another binding partner, also called a capture element, integrated into the detection zone. Example binding partners included in conjugates include antibodies, antigens, analyte or analyte-mimics, protein, etc.

Optionally located in the fluid flow path, before or after the reagent zone 312 and before the detection zone 318 is a reagent addition zone (not shown). The reagent addition zone can allow the addition of a reagent externally from the device 300. For example, the reagent addition zone may be used to add an interrupting reagent that can be used to wash the sample and other unbound components present in the fluid flow path into a wicking zone 324. In a preferred embodiment, the reagent addition zone is located after the reagent zone 312.

Downstream from the reagent zone 312 and along the folded fluid path defined by the flow channel 317 is the detection zone 318 which is in fluid communication with the reagent zone. The detection zone 318 may include projections or micropillars, such as those as described above. Also as noted above, these projections are preferably integrally molded into the substrate from an optical plastic material such as Zeonor, such through an injection molding or embossing process. The width in the flow path in the detection zone 318 is typically on the order of 0.5-4 mm and preferably on the order of about 2 mm, although others can be prepared on the order of about 1 mm, provided sufficient signal for a suitable detection instrument, such as a fluorimeter, can be read even if the reagent plume does not cover the entire width of the detection zone.

The detection zone 318 is where any detectable signal can be read. In a preferred embodiment and attached to the projections in the detection zone 318 are capture elements. The capture elements can hold binding partners for the conjugate or complexes containing the conjugate, as described above. For example, if the analyte is a specific protein, the conjugate may be an antibody that will specifically bind that protein to a detection element such as fluorescence probe. The capture element could then be another antibody that also specifically binds to that protein. In another example, if the marker or analyte is DNA, the capture molecule can be, but is not limited to, synthetic oligonucleotides, analogues, thereof, or specific antibodies. Other suitable capture elements include antibodies, antibody fragments, aptamers, and nucleic acid sequences, specific for the analyte to be detected. A non-limiting example of a suitable capture element is a molecule that bears avidin functionality that would bind to a conjugate containing a biotin functionality. The detection zone can include multiple detection zones. The multiple detection zones can be used assays that include one or more markers. In the event of multiple detection zones, the capture elements can include multiple capture elements, such as first and second capture elements. The conjugate can be pre-deposited on the assay device, such as by coating in the reagent zone. Similarly, the capture elements can be pre-deposited on the assay device on the detection zone. Preferably, both the detection and capture elements are pre-deposited on the assay device, or on the reaction zone and detection zone, respectively.

Capture elements, such as antibodies in the detection zone (such as by coating); and a labeled conjugate material that is also capable of participating in reactions that will enable determination of a concentration of analyte, are preferably deposited on the device in the reagent zone, wherein the labeled conjugate material carries a label for detection in the detection zone.

After the sample has been delivered to the sample addition zone 308, it will encounter the reagent zone 312. After the sample has flowed through and interacted with the reagent zone 312 and optionally the reagent addition zone, the sample and a reagent plume will be contained in the fluid flow. The reagent plume can contain any of the reagent materials that have been dissolved in the reaction zone 312 or those added through the optional reagent addition zone. The reagent plume can include the conjugate having both the detection element and binding partner, in which case it is often referred to as a conjugate plume.

Downstream from the detection zone 318 along the folded fluid path is the wicking zone 324 in fluid communication with the detection zone. The wicking zone 324 is an area of the assay device 300 with the capacity of receiving liquid sample and any other material in the flow path, e.g. unbound reagents, wash fluids, etc. The wicking zone 324 provides a capillary force to continue moving the liquid sample through and out the detection zone of the assay device. The wicking zone can include a porous material such as nitrocellulose or preferably is a non-porous structure defined by projections as described previously. The wicking zone can further include non-capillary fluid driving means, such as using evaporative heating or a pump. Further details of wicking zones as used in lateral flow assay devices according to the present invention are found in patent publications US 2005/0042766 and US 2006/0239859, both of which are incorporated herein by reference in their entireties.

Preferably, the entirety of the flow path including the sample addition zone, the detection zone and the wicking zone includes projections substantially vertical in relation to the substrate, and having a height, diameter and reciprocal spacing capable of creating lateral capillary flow of the sample in the flow path.

Components of the lateral flow assay devices (i.e., a physical structure of the device whether or not a discrete piece from other parts of the device) described herein can be prepared from copolymers, blends, laminates, metallized foils, metallized films or metals. Alternatively, device components can be prepared from copolymers, blends, laminates, metallized foils, metallized films or metals deposited one of the following materials: polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicon containing polymers, glass, and ceramic materials. Alternatively, components of the device can be made with a plastic, elastomer, latex, silicon chip, or metal; the elastomer can comprise polyethylene, polypropylene, polystyrene, polyacrylates, silicon elastomers, or latex. Alternatively, components of the device can be prepared from latex, polystyrene latex or hydrophobic polymers; the hydrophobic polymer can comprise polypropylene, polyethylene, or polyester. Alternatively, components of the device can comprise TEFLON®, polystyrene, polyacrylate, or polycarbonate. Alternatively, device components are made from plastics which are capable of being embossed, milled or injection molded or from surfaces of copper, silver and gold films upon which may be adsorbed various long chain alkanethiols. The structures of plastic which are capable of being milled or injection molded can comprise a polystyrene, a polycarbonate, or a polyacrylate. In a particularly preferred embodiment, the lateral flow assay devices are injection molded from a cyclo olefin polymer, such as those sold under the name Zeonor®. Preferred injection molding techniques are described in U.S. Pat. Nos. 6,372,542, 6,733,682, 6,811,736, 6,884,370, and 6,733,682, all of which are incorporated herein by reference in their entireties.

The defined flow path of the assay devices described herein, including device 300, can include open or closed paths, grooves, and capillaries. Preferably the flow path comprises a lateral flow path of adjacent projections, having a size, shape and mutual spacing such that capillary flow is sustained through the flow path. In one embodiment, the flow path is in a channel within the substrate having a bottom surface and side walls. In this embodiment, the projections protrude from the bottom surface of the channel. The side walls may or may not contribute to the capillary action of the liquid. If the sidewalls do not contribute to the capillary action of the liquid, then a gap can be provided between the outermost projections and the sidewalls to keep the liquid contained in the flow path defined by the projections. Preferably, the reagent that is used in the reaction zones 312 and the capture members or detection agent used in the detection zones 318 is bound directly to the exterior surface of the projections used in the herein described assay device 300.

Figure 2:
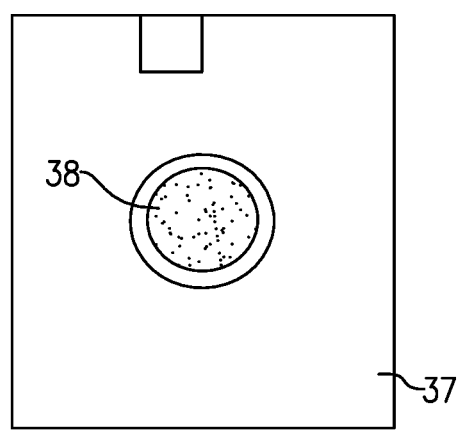
FIG. 2 is a top plan view of a known thin film analytical test element used in the automated clinical analyzer of FIG. 1.
Figure 6:
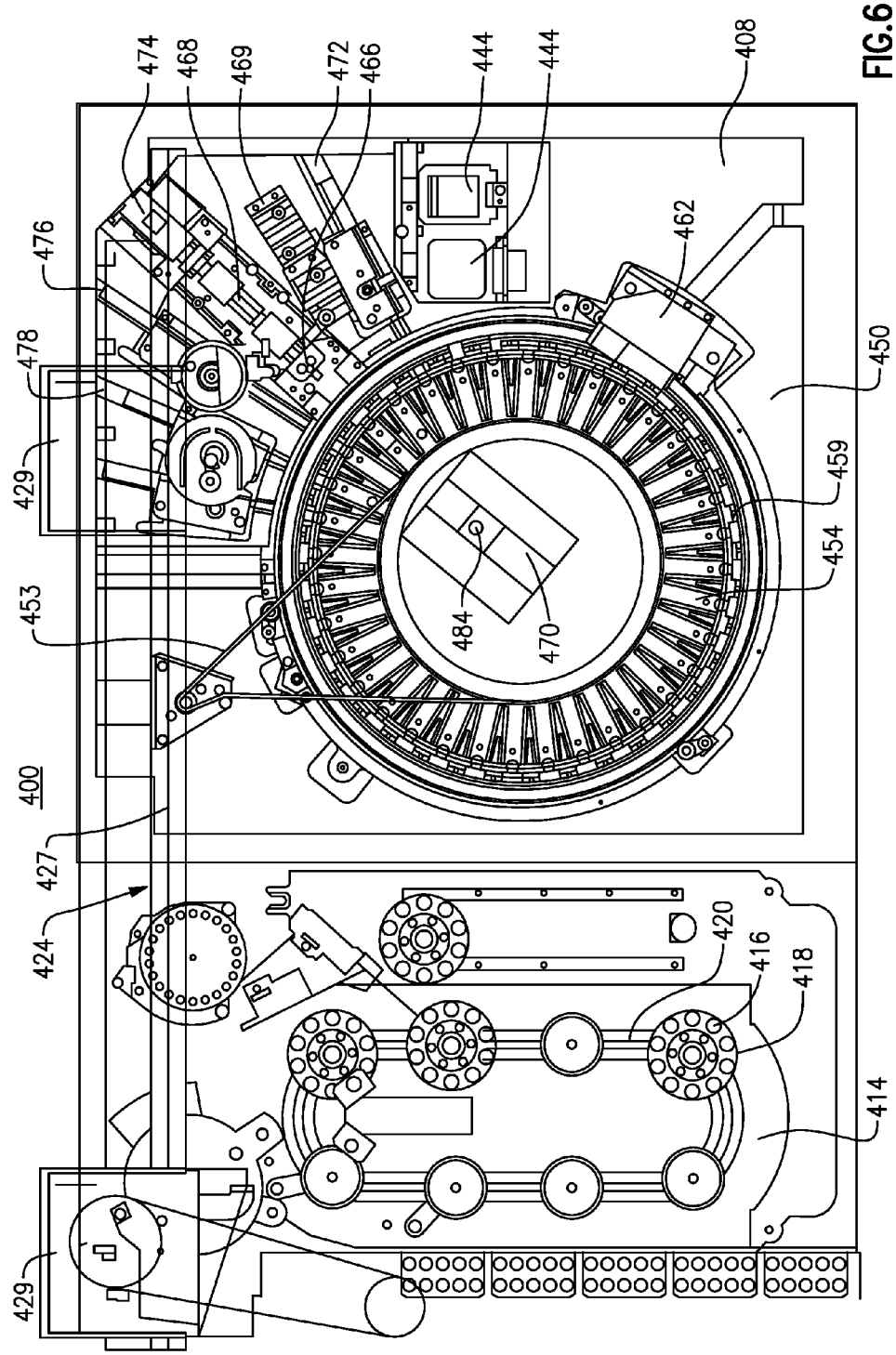
FIG. 6 is a top plan view of an automated clinical analyzer that is configured to interchangeably utilize both lateral flow assay devices and thin film analytical slide test elements.
Figure 7:
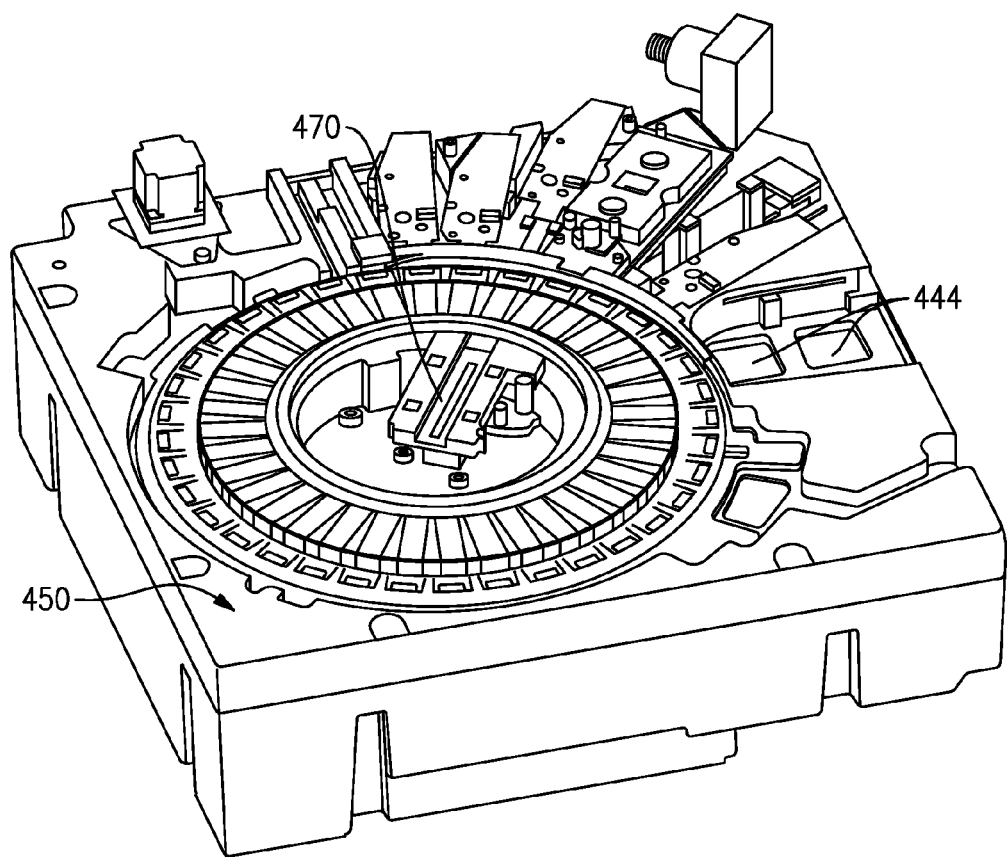
FIG. 7 depicts a partial front perspective view of the automated clinical analyzer of FIG. 6 and more specifically the incubator assembly thereof.
Figure 8:
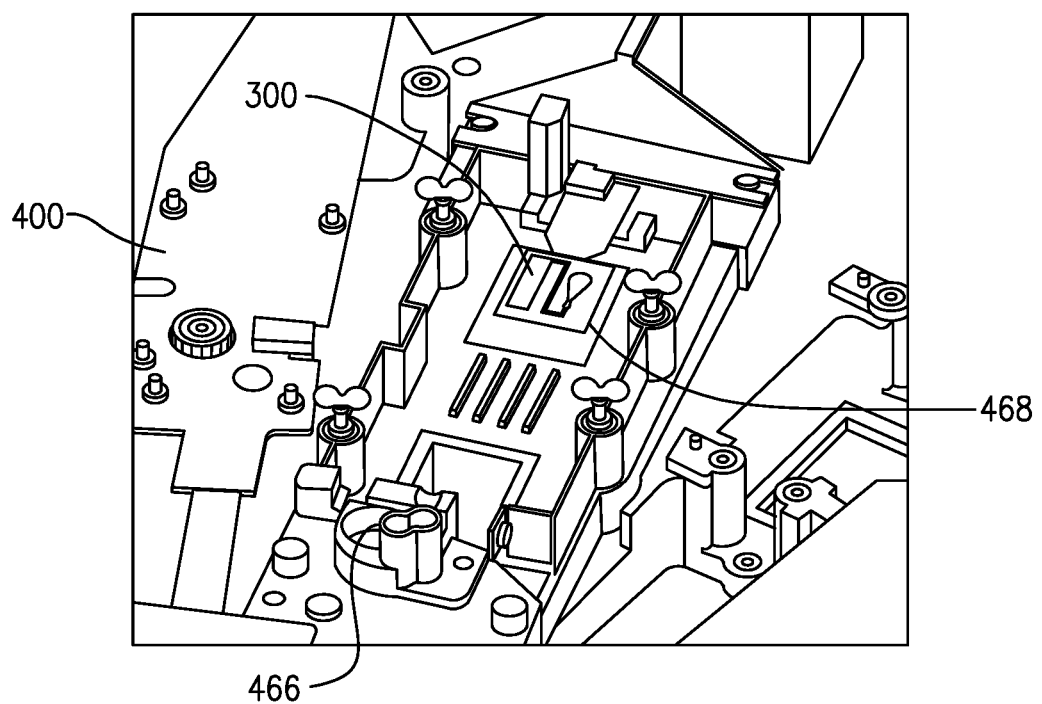
FIG. 8 is an enlarged top view of the automated clinical analyzer of FIGS. 6 and 7, depicting the loading/staging of a lateral flow assay device for use therein.
Figure 9:
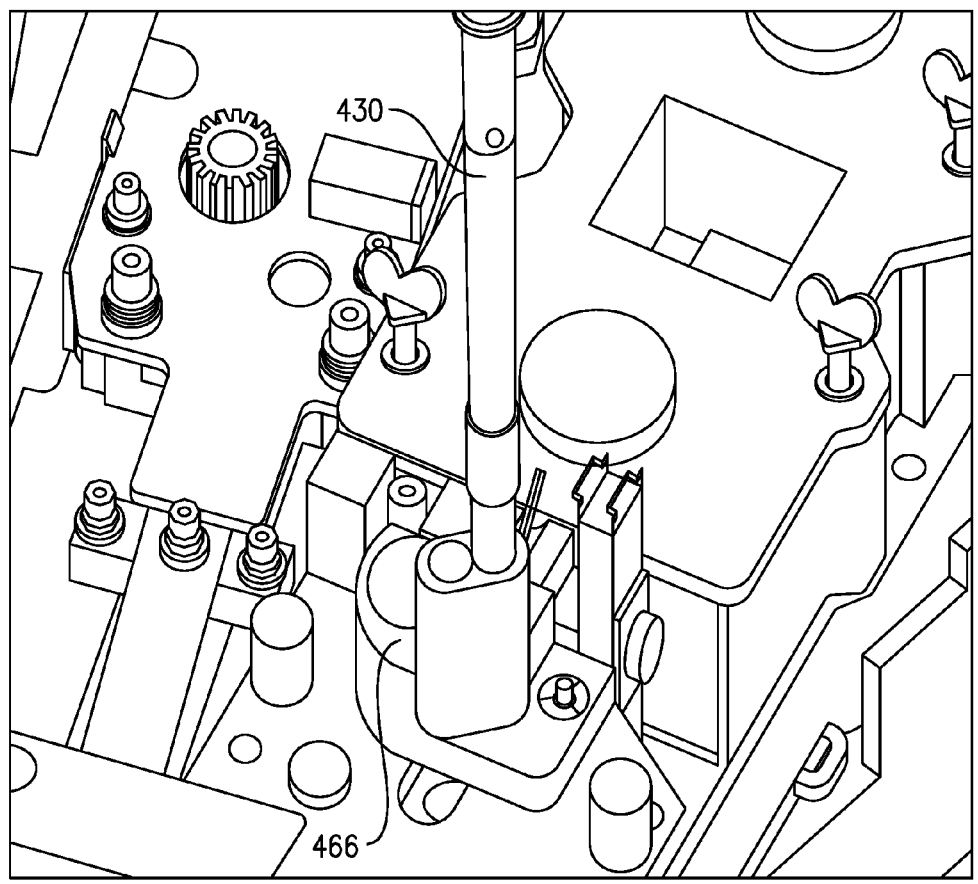
FIG. 9 is an enlarged top view of a portion of the automated clinical analyzer of FIGS. 6-8, illustrating the metering of sample onto a lateral flow assay device at a dispensing station of the analyzer.

Referring to FIG. 6, an automated clinical analyzer 400 is herein described in accordance with one exemplary embodiment, the exemplary analyzer being configured for interchangeably handling and processing both analytical test elements 36, such as those in FIG. 2 and lateral flow assay devices 300, such as those depicted in FIG. 5. More specifically, the clinical analyzer 400 is defined by a housing or enclosure 408 that retains a plurality of components. These components include a sample supply 414 that retains a plurality of sample receptacles or test tubes 416 in carrier members 418 that are moved along an endless belt 420 over an ovate transport path. A metering mechanism 424 includes a metering rail 427 aligned with the sample supply 414 and retaining a translatably movable metering head 429 having an attached proboscis 430, FIG. 9, that is vertically movable to aspirate a predetermined quantity of sample from one of the sample receptacles 416 at an aligned aspiration station.

An incubator assembly 450 is disposed in relation to the metering rail 427, including a pair of concentric rotor assemblies that are independently rotatable about a center axis, such as through a belt drive 453. The incubator assembly 450 according to this embodiment is defined by a plurality of independently rotatable rings 454, 459, each of the rings including a plurality of slots or receiving stations that are sized for retaining either a thin film slide test element or a lateral flow assay device 300, as discussed herein. According to this embodiment, a predetermined number (N) receiving slots are provided wherein the incubator housing further includes a cover (not shown). An electrometer 462 is disposed adjacent one of the rings 454 of the incubator 450 and a colorimeter (not shown) is disposed beneath another of the independently rotatable rings 459 to enable testing of thin film analytical test elements 36, FIG. 2, and permit interchangeability therein, as needed. The incubator 450 can be further equipped to permit immunorate testing of thin film analytical test elements 36, FIG. 2, by movement of the slide elements to the interior of the inner ring 459. A plurality of reciprocating pusher blade assemblies 472, 474, 476, 478 and 479 are disposed about the outer periphery of the incubator housing in spaced relation, these latter assemblies enabling thin film analytical test elements 36 to be radially moved between the rotatable rings 454, 459. A metering station 466 is disposed in relation to the exterior of the incubator housing adjacent a staging station 468 in which test elements are positioned prior to metering and loading into the incubator 450 for processing. A shuttle mechanism 469 is disposed for moving test elements discharged from a storage cartridge (not shown) disposed in a supply slot 444 to the staging station 468.

One of the reciprocating pusher blade assemblies 474 is disposed to push at least one test element 36, FIG. 2, from the staging station 468 to the metering station 466 to receive a quantity of sample and from the metering station to one of the rings 454, 459 of the incubator for processing. As to the preceding aspects of the sample supply 414, metering mechanism 424 and incubator assembly 459, each of them are as described or substantially similar to those described in greater detail in previously incorporated U.S. Pat. Nos. 7,250,303 and 7,855,084B2, and in which the above noted features specific to the incubator assembly 450 are further described in greater detail in U.S. Pat. No. 7,312,084 and in which the pusher blade assemblies are described in general in U.S. Pat. No. 5,073,342, each also herein incorporated in its entirety. In this regard, the system described to this point is substantially similar to that previously described in terms of the dry chemistry "side" of the combinational analyzer described in the above-referenced U.S. Pat. No. 7,250,303.

In this regard, the lateral flow assay devices 300 are sized substantially to be equivalent to that of the previously known analytical thin film test elements 36, FIG. 2. The herein described automated clinical analyzer 400 is further configured to enhance capability of same to interchangeably incorporate and process lateral flow assay devices 300 in addition to the test elements 36, as discussed herein. Alternatively, however, the automated clinical analyzer can be configured to separately incorporate lateral flow assay devices and thin film analytical test elements or operate as a stand-alone device that solely receives and processes lateral flow assay devices. Alternatively and according to another version, the apparatus can further be equipped with a wet chemistry analytical system, as described in previously incorporated U.S. Pat. No. 7,250,303. Combinations of each described variant are also contemplated within the inventive aspects discussed herein.

Figure 12:
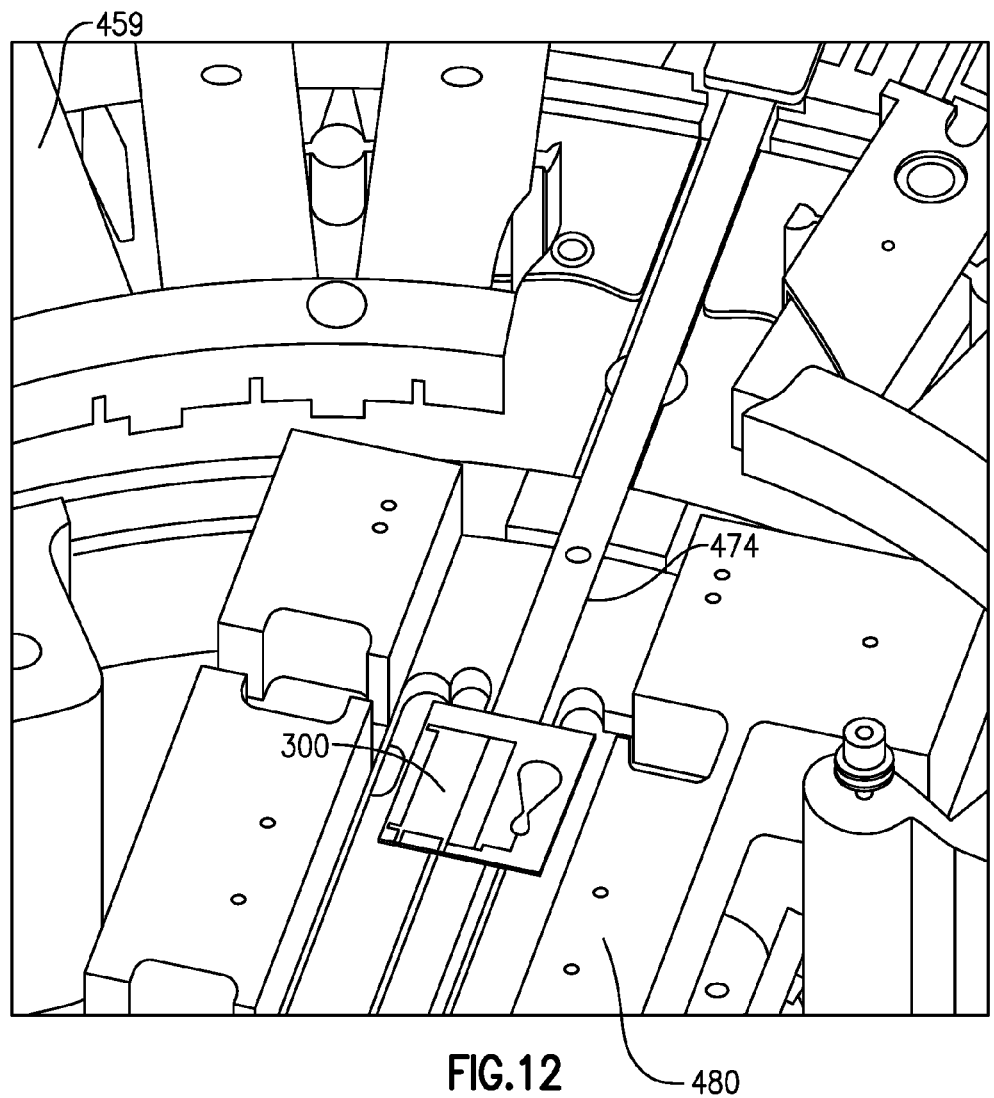
FIG. 12 illustrates the loading of the lateral flow assay device from the incubator assembly to a testing station of the automated clinical analyzer.
Figure 13:
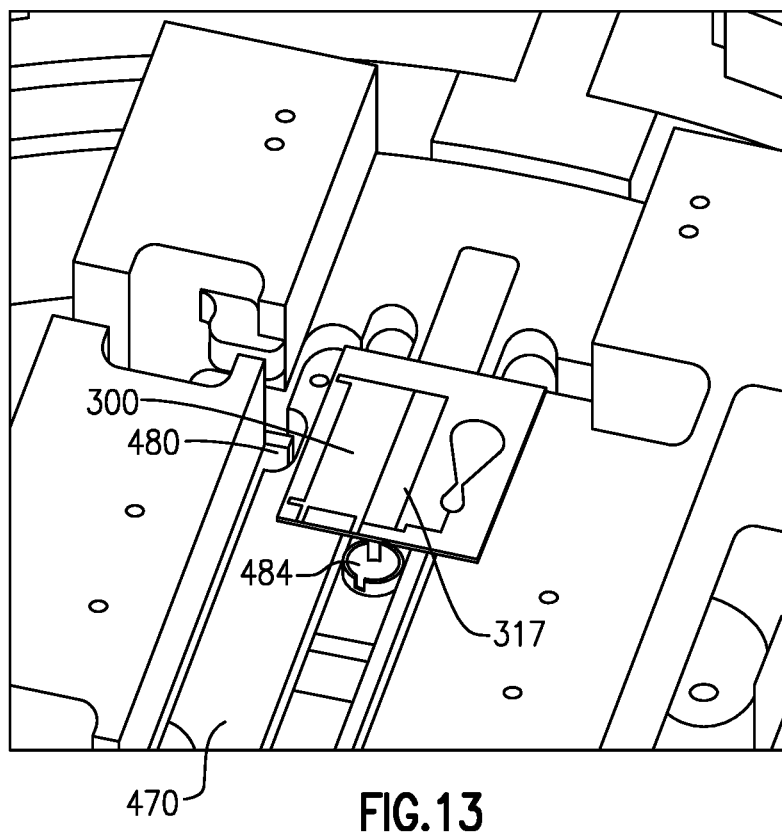
FIG. 13 is an enlarged version of FIG. 12, illustrating the alignment of the detection/testing instrument of the automated clinical analyzer relative to the lateral flow assay device.

According to this exemplary embodiment, a detection instrument capable of detecting the perceivable signal of the detection area 318 of the lateral flow assay device 300, and more specifically a fluorimeter 470, is disposed substantially in the center of the incubator housing adjacent the innermost ring 454 thereof and aligned to linearly scan lateral flow assay devices 300 that are caused to be positioned within an adjacent test station 480, FIG. 12. The fluorimeter 470 is equipped with a laser 484 used to optically scan the devices one at a time along a portion of the fluid flow path and more preferably along the linear portion 317 of the flow channel separating the sample addition zone 308 and the wicking zone 324 and preferably containing the detection zone 318 and depending on the construction of this element, at least one reaction zone 312. This specific positioning of the incubator is useful in that the reciprocating pusher blade assembly 474 was previously configured to advance a dry slide test element 36 into an IR wash module previously disposed in the center of the incubator. For purposes of this embodiment, the wash module of the existing analyzer is removed with the fluorimeter 470 assuming this location. It will be readily apparent that there are various alternative positions that the above-noted detection instrument could assume. Certain of these alternatives are discussed in a later portion of this description.

The test elements/assay devices 36, 300 for purposes of this description are each separately maintained within storage receptacles or cartridges (not shown) that are sized to retain a predetermined number of elements/devices in a stacked format. According to this specific embodiment and as noted above, the overall perimeter and thickness parameters of the analytical test element 36 of FIG. 2 and the lateral flow assay device 300 of FIG. 5 are substantially identical and therefore interchangeability is provided in terms of accommodation throughout processing. Each storage cartridge is disposed within at least one vertically aligned storage slot of the analyzer 400. According to this specific embodiment, a pair of parallel storage slots 444 are provided.

As noted, the processing of dry-slide analytical test elements 36, FIG. 2, is generally known and as previously described herein. The following describes the incorporation of lateral flow assay devices 300, which are dispensed one at a time from a lower opening of a storage cartridge (not shown) as retained within at least one of the supply slots 444. These devices 300 are shuttled using the mechanism 469 or similar means into the staging station 468. From this position, the reciprocating pusher blade assembly 474 engages a side or lateral edge of the device 300 in order to translatably move same. The staging station 468 according to this embodiment includes a pair of axially disposed slots enabling a pair of assay devices 300 from respective storage cartridges to be retained in side by side relation and in which the reciprocating pusher blade assembly 474 is configured to advance the assay devices 300 radially to the metering station 466, the latter having at least one opening sized to receive the proboscis and attached metering tip of the metering head 429, which can be lowered therein.

In terms of overall operation, at least one storage cartridge (not shown) can be loaded with thin film analytical test elements 36, FIG. 2, while at least one other storage cartridge (not shown) can be filled with a predetermined quantity of lateral flow assay devices 300, such as those previously described herein.

Referring to FIGS. 7-13, one exemplary sequence is herein described involving the testing of at least one lateral flow assay device 300 in the clinical analyzer 400. First and referring to FIG. 7, a pair of storage cartridges (not shown) are loaded into each of the supply slots 444 of the analyzer 400, at least one storage cartridge containing a plurality of lateral flow assay devices 300. If selected and according to FIG. 8, a lateral flow assay device 300 can be removed from the lower end of a retained storage cartridge and shuttled laterally into a slot of the staging station 468 sized to retain the device, the slot being adjacent the dispensing or metering station 466 of the analyzer 400. From this position and referring to FIG. 9, the lateral flow assay device 300 is further shuttled using the pusher blade assembly 474, FIG. 6, into the metering station 466 such that the lateral flow assay device is positioned within the confines of a metering block and in which the sample addition zone 308 is positioned directly beneath a metering opening. In parallel, the analyzer 400 has already caused the metering truck 44 to pick up a disposable metering tip from a tip supply of the analyzer for attachment onto the proboscis and aspirated a quantity of sample from one of the test receptacles 416 at the sample supply 414. The proboscis 430, partially shown, is moved into position along the metering rail 427, FIG. 6, according to this embodiment and lowered into the metering opening. A predetermined volume of sample (10-15 microliters) is then deposited onto the sample addition area 308 of the lateral flow assay device 300.

Based on the design of the instant lateral flow assay device 300, the application of sample to the sample addition area 308 and particularly the upwardly extending projections spontaneously induces lateral capillary flow of the dispensed patient sample along the defined flow path. According to this element design, sample flows outwardly through an optional filter and through the defined projections of the sample addition area 308 under the capillary force created along the flow path extending through the reaction zone 312. As the fluid sample first engages the detection conjugate or other reagent, the sample begins to dissolve this conjugate, thereby creating a perceivable plume indicative of the process flow, such as a conjugate plume, as previously discussed. The sample and related material advance through the optional reaction adding zone and the defined flow channel 317 towards the detection zone 318 and the wicking zone 324 of the assay device 300. The fluid sample continues to flow along the flow path through the channels defined therein and along each intermediate reaction area against reactants or other moieties that are bound or otherwise attached to the projections, enabling a reaction to take place, which can be detected along a defined linear path by the fluorimeter 470 or other optical or suitable test/detection instrument, as discussed herein, and in which the sample continues to advance to the wicking area 324, the latter being sized to receive the volume of fluid dispensed.

Figure 10:
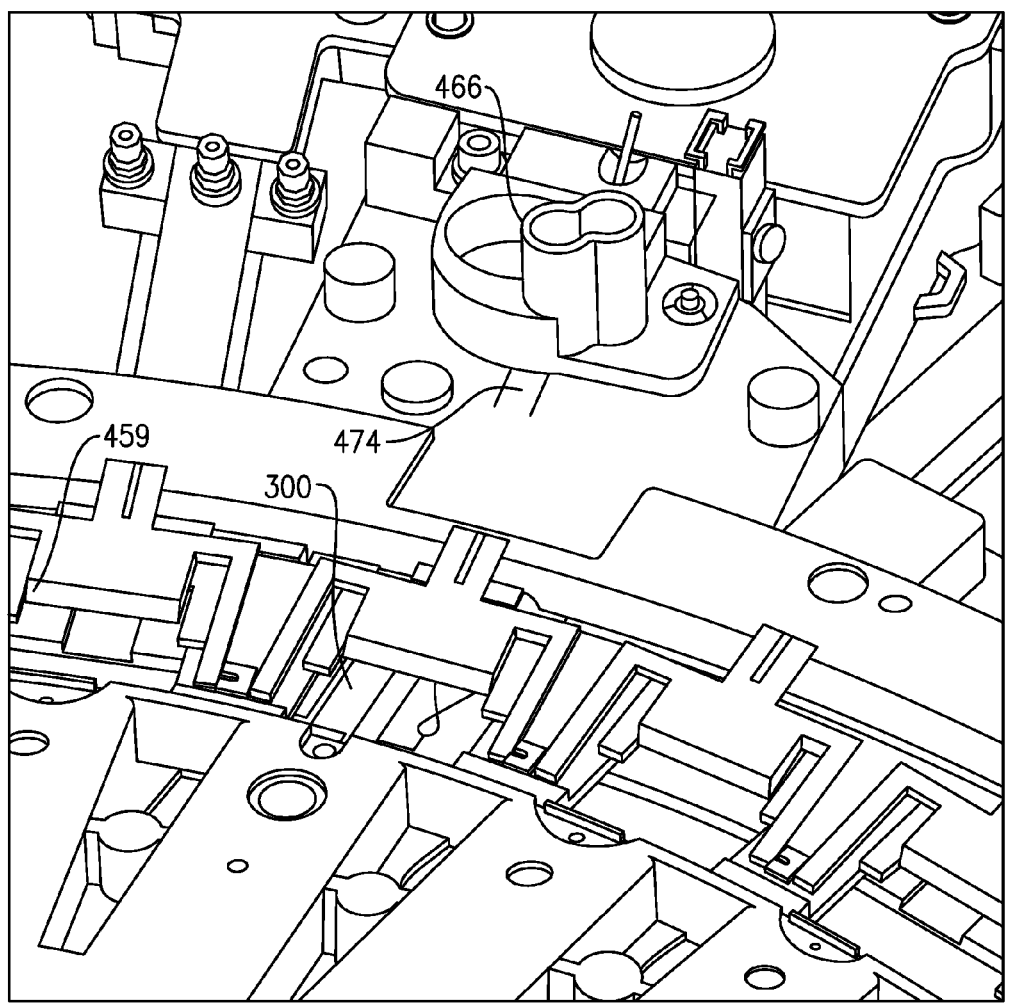
FIG. 10 illustrates an enlarged top view of a portion of the automated clinical analyzer of FIGS. 6-9, depicting the loading of a lateral flow assay device into an outer ring of the incubator assembly.
Figure 11:
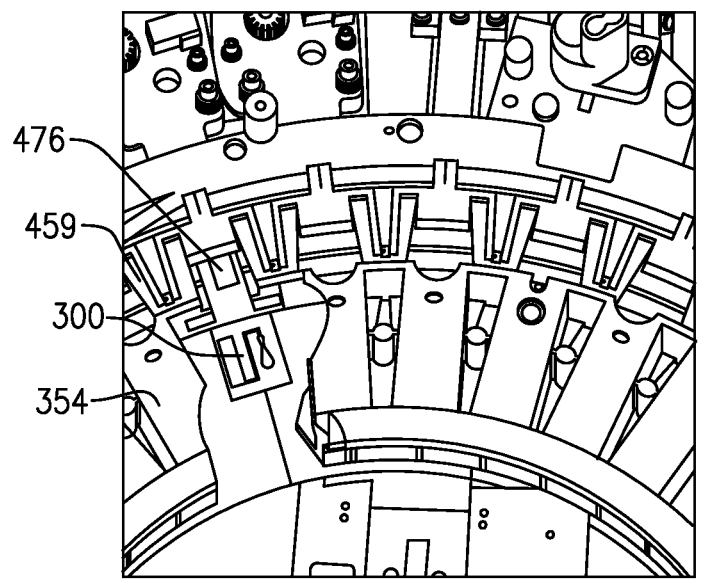
FIG. 11 illustrates another enlarged top view of a portion of the automated clinical analyzer of FIGS. 6-10, depicting the movement of the lateral flow assay device from the outer ring depicted in FIG. 10 to an inner ring of the incubator assembly.

As reaction(s) are occurring based on the addition of sample to the lateral flow assay device 300 and referring to FIG. 10, the lateral flow assay device can be radially positioned from the metering station 466 to a slot provided on the outer ring 459 of the incubator 450 after a predetermined dwell time using the pusher blade assembly 474. Following a few cycles (rotations) and as shown in FIG. 11, the lateral flow assay device 300 can be further advanced into the inner ring 454 of the incubator 450 using one of the plurality of adjacent reciprocating pusher blade assemblies 476 that is disposed about the outer periphery of the incubator assembly 450. The lateral flow assay device 300 can further be radially advanced within the inner ring 459 to an inner radial position, depending on the number and types of tests to be performed on the assay device 300. Following a predetermined incubation time (e.g., 5 minutes, 10 minutes, etc.) and referring to FIGS. 12 and 13, the pusher blade assembly 474 can further cause the lateral flow assay device 300 to be pushed radially inward and into the test station 480 adjacent the scanning laser 484 of the fluorimeter 470. Once situated in this station, the assay device 300 is aligned in order to permit sequential optical scanning of the contained sample and reactants along a portion 317 of the flow path that aligns the detection area 318 of the assay device 300 with the scanning laser 484 of the fluorimeter 470 allowing analytical test or detection results can be therefore be provided in real time. In the present embodiment, the scanning laser 484 of the fluorimeter 470 takes fluorescence measurements over the reaction or detection zone in which the results are available or further analysis by prediction algorithms processed in an on-board computer. Following scanning by the fluorimeter 470, the lateral flow assay devices 300 are caused to drop one at a time through a vertically disposed exit chute (not shown) of the incubator assembly 450 and are discarded.

Figure 14:
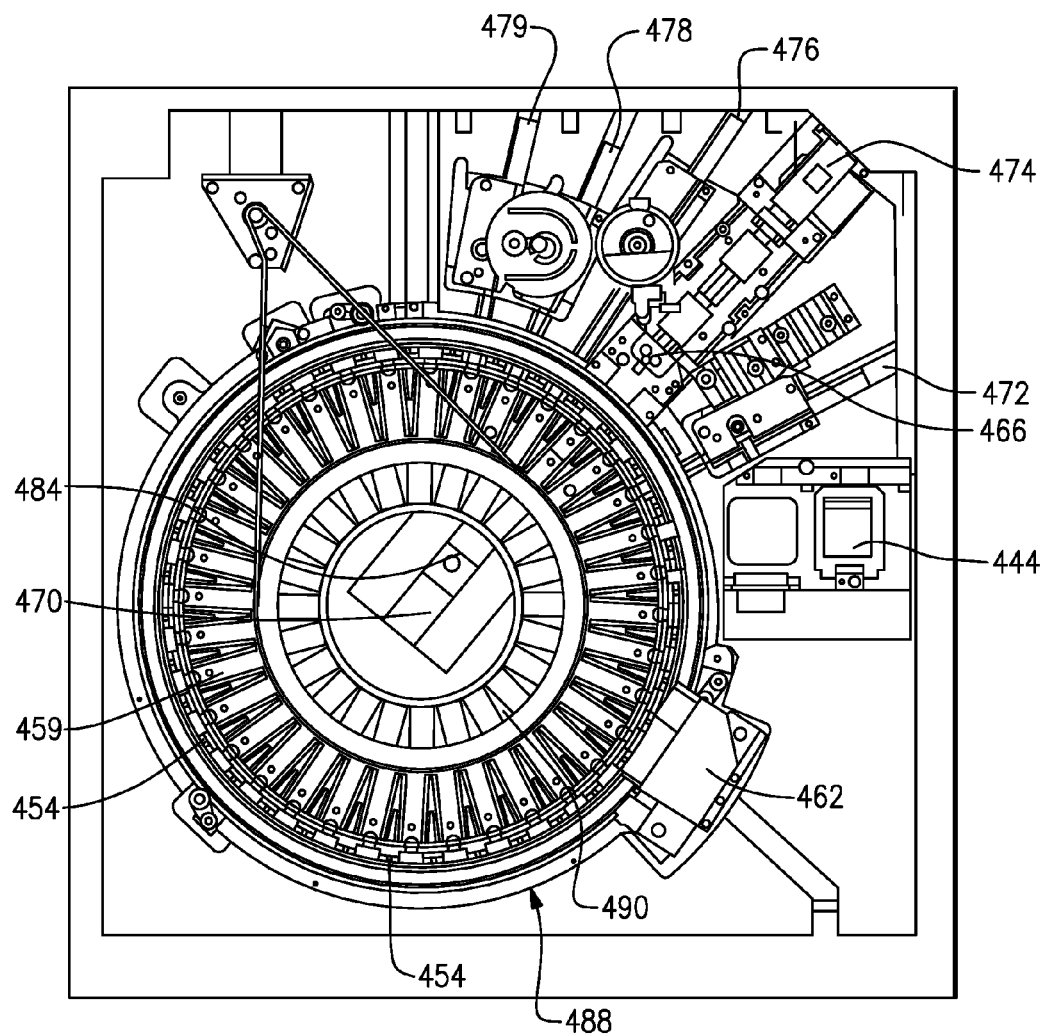
FIG. 14 is a top view of a portion of another automated clinical analyzer, including an incubator assembly made in accordance with another exemplary embodiment.

Other variations are possible within the framework of these described concepts. For example and referring to FIG. 14 in which similar parts are labeled with the same reference numerals, the incubator assembly 488 can be alternatively constructed to include a separate interior ring 490 having a predetermined number of retaining stations or slots with appropriate temperature and humidity controls, this latter ring being used specifically for lateral flow assay devices such as those previously described or other designs, for example, those having different form factors as compared to conventional thin film slide analytical test elements 36, FIG. 2. The assay devices can be directly loaded into the interior ring 490 or initially loaded using the pusher blade assembly into the outer ring 454 and subsequently advanced radially inwardly using any of the pusher blade assemblies 472, 476, 478 and 479 to the interior ring. As in the preceding, the pusher blade assembly 474 can be utilized to advance assay devices from the interior ring to the reading station 480 prior to having optical or other detection measurements made thereon.

Figure 15:
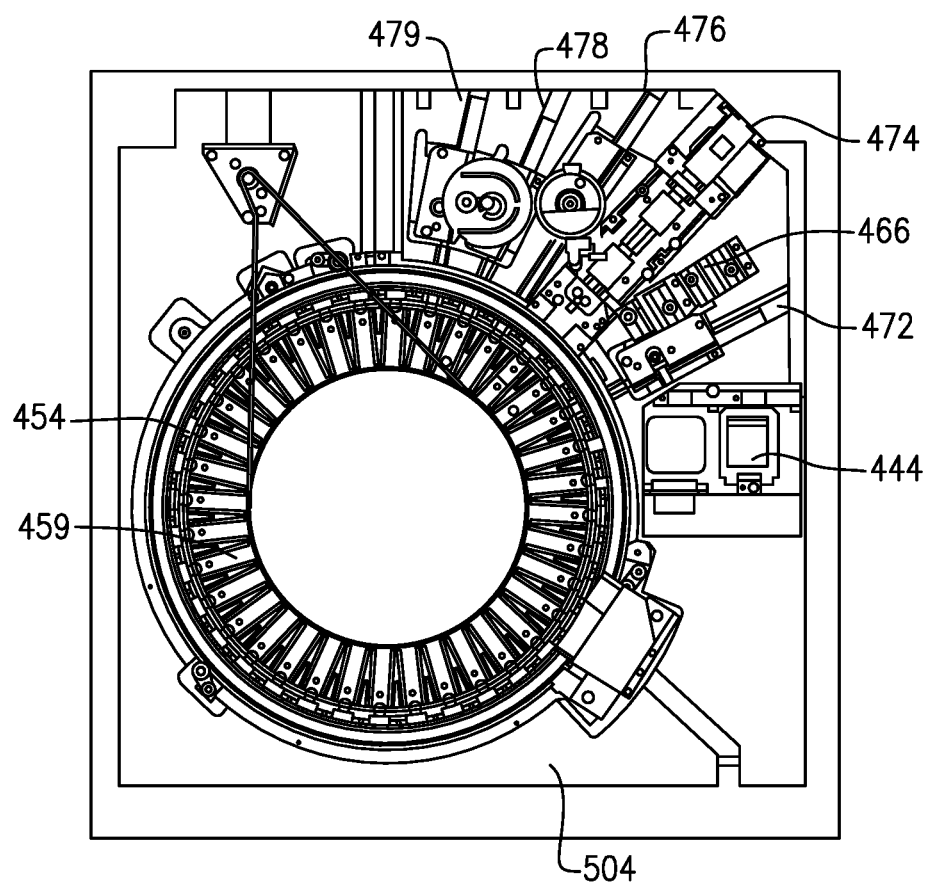
FIG. 15 is a top view of a portion of yet another automated clinical analyzer, and particularly another alternative incubator assembly design.

Still other variations are also contemplated herein. For example and referring to FIG. 15, a separate ring and/or the testing/detection instrument (i.e., fluorimeter) can either be planar to the inner and outer rings 454, 459 of the incubator 504 or can, for example, be disposed either above or below the horizontal plane defined thereby. In this construction, for example, an elevator assembly (not shown) can be included that permits the loading and unloading of assay devices, as needed. One exemplary elevator design as used in an incubator with portions defined on different horizontal planes is described in U.S. Pat. No. 5,419,871 to Muszak et al, the entire contents of this disclosure being incorporated herein.

Still other variations are possible employing the concepts described herein. For example, a fluorimeter or other suitable detection/reading instrument can be disposed relative to an already existing ring of the incubator assembly. Other similar variations are herein contemplated herein.

Figure 16:
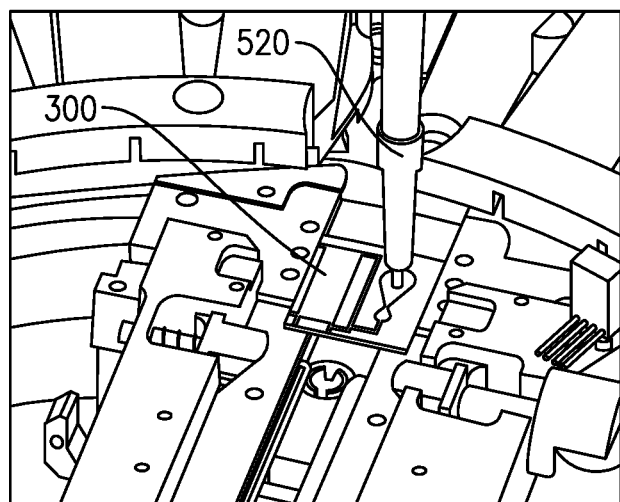
FIG. 16 is a partial top perspective view of a wash operation in an automated clinical analyzer involving a lateral flow assay device and in accordance with another embodiment.

As noted, the herein described lateral flow assay devices can be designed to include features to enable additional processing, such as at least one reaction adding zone. Referring to FIG. 16 and according to one exemplary version, a lateral flow assay device may optionally include at least one wash area adjacent the sample addition area of the device, which can be used, for example in the conduction of assays involving whole blood as a sample. A metering head 520 can be lowered by known means to add wash fluid to a reagent adding zone of a suitable lateral flow assay device.

PARTS LIST FOR FIGS. 1-16

10 analyzer, clinical diagnostic
14 primary sample supply
18 sample receptacles
22 primary metering mechanism
23 sample carrier members
26 metering rail
30 metering truck/head
34 incubator assembly
36 thin-film slide element (analytical test element)
39 pusher blade
40 auxiliary sample supply
42 secondary metering mechanism
44 metering truck/head
52 reagent wheel
54 reagent containers
56 incubator assembly
58 reaction vessel loader
60 micro-tip loader
64 reaction vessel
68 metering station
80 "dry" chemistry analytical system
90 "wet" chemistry analytical system
100 lateral flow assay device
108 substrate
112 projections
115 bordering line
118 sample addition zone
120 reaction zone
124 detection zone
130 wicking zone
200 lateral flow assay device
208 substrate
212 projections
214 sample addition zone
215 bordering line
216 reagent zone
218 detection zone
230 wicking zone
234 hydrophilic cover
300 lateral flow assay device
304 substrate
308 sample addition zone
312 reagent zone
317 flow channel
318 detection zone
324 wicking zone
400 clinical analyzer
408 housing
414 sample supply
416 test receptacles or test tubes
418 carrier members
420 endless belt
424 metering mechanism
427 metering rail
429 metering head
430 proboscis
442 dispensing station
444 storage slots
446 opening
448 opening
450 incubator assembly
453 belt drive
454 inner ring, incubator
459 outer ring, incubator
462 electrometer
466 metering station
468 staging station
469 shuttle mechanism
470 fluorimeter
472 reciprocating pusher blade assembly
474 reciprocating pusher blade assembly
476 reciprocating pusher blade assembly
478 reciprocating pusher blade assembly
479 reciprocating pusher blade assembly
480 reading station
484 laser, scanning
488 incubator assembly
490 ring
504 incubator assembly
520 metering head It will be appreciated that numerous other modifications and variations will be readily apparent to one of sufficient skill in the field that encompass the inventive concepts described herein, as well as those that are also defined by the following listed claims. For example, the herein described lateral flow assay devices can also be used in conjunction with point-of-care (POC) analyzers or other apparatus. According to at least one version, a lateral flow assay device could be interchangeably used in both POC and mainframe clinical analyzer applications.

The invention claimed is:

1. A method for processing analytical test elements in a clinical analyzer, said method comprising the steps of:
   introducing a first plurality of analytical test elements into said clinical analyzer, said first plurality comprising lateral flow assay devices each comprising a support, at least one sample addition area, at least one reagent area, at least one detection area, and at least one wicking area, each of said areas being fluidly interconnected to one another to define at least one linear fluid flow path;
   dispensing a volume of sample onto the sample addition area of at least one of said plurality of lateral flow assay devices, wherein the sample is caused to move along the at least one fluid path under capillary action and in which a detectable signal is produced when the moving sample is combined with material in the reaction zone for detection of the detectable signal in the at least one detection area;
   advancing the at least one lateral flow assay device into an incubator of the clinical analyzer;
   incubating said at least one lateral flow assay device;
   aligning the at least one lateral flow device with a fluorimeter disposed within the incubator; and
   scanning a linear portion of the detection area of the at least one lateral flow device within the incubator for the presence of the detectable signal from said at least one lateral flow assay device using the fluorimeter.

2. A method as recited in claim 1, wherein said introducing step includes the step of loading a storage cartridge retaining the plurality of said lateral flow assay devices in stacked relation in the storage cartridge into the analyzer.

3. A method as recited in claim 1, wherein said dispensing step includes the step of aspirating a quantity of sample from a sample supply of said analyzer using a metering mechanism and dispensing at least a portion of said aspirated sample onto the sample addition area of said at least one lateral flow assay device.

4. A method as recited in claim 1, wherein said advancing step includes the step of shuttling said at least one lateral flow assay device from a dispensing station into a receiving station of said incubator.

5. A method as recited in claim 1, wherein said shuttling step is performed by a reciprocating pusher blade assembly.

6. A method as recited in claim 1, wherein each said lateral flow assay device includes a plurality of projections extending upwardly from a top surface of said support, said plurality of projections having a center to center spacing and having height and diameter dimensions configured to enable the capillary flow of sample applied to said sample addition area along the at least one fluid flow path.

7. A method as recited in claim 1, including the additional step of introducing a second plurality of analytical test elements to the clinical analyzer, said second plurality comprising a plurality of thin-film slide elements, said method further including the steps of dispensing a quantity of sample onto a sample addition area of at least one of the plurality of said thin-film slide elements, sequentially advancing the at least one thin-film slide element into the incubator, incubating the at least one thin-film slide elements and detecting of at least one test result relating thereto.

8. A method as recited in claim 7, including the further step of interchangeably handling the processing of the first and second pluralities of analytical test elements by said incubator of the clinical analyzer.

9. A method as recited in claim 1, including the additional step of providing a wet chemistry assay system on said clinical analyzer.

10. A method as recited in claim 1, in which the analyzer is at least one of a point of care analyzer and an automated clinical analyzer.

11. A method as recited in claim 4, in which the incubator is defined by a pair of concentric rings, each of the rings including receiving stations disposed circumferentially about a center axis, the rings being rotatable about the center axis.

12. The method as recited in claim 11, in which the fluorimeter is disposed within and adjacent the center of a housing of the incubator, the method including the steps of initially receiving the at least one lateral flow device in a receiving station of an outer ring of the incubator, shuttling the at least one lateral flow device to a receiving station in the inner ring, and aligning the at least one lateral flow device for detection by scanning of the fluorimeter for detection of the detectable signal.

13. The method as recited in claim 12, wherein the material in the reagent area produces a fluorescent signal when mixed with the moving sample, the method including the step of using the fluorimeter to detect the fluorescent signal in the detection zone of the at least one lateral flow device.

* * * * *